United States Patent

Matsumoto et al.

[11] 4,306,087
[45] Dec. 15, 1981

[54] HYDROFORMYLATION OF OLEFINIC COMPOUNDS

[75] Inventors: Mitsuo Matsumoto; Masuhiko Tamura, both of Kurashiki, Japan

[73] Assignee: Kuraray Co., Ltd., Kurashiki, Japan

[21] Appl. No.: 175,842

[22] Filed: Aug. 6, 1980

[30] Foreign Application Priority Data

Aug. 10, 1979 [JP] Japan ................. 54/102579

[51] Int. Cl.$^3$ ................. C07C 45/50; C07C 47/02
[52] U.S. Cl. ................. 568/454; 252/431 P
[58] Field of Search ............ 568/454, 882, 909, 454, 568/431 P; 252/431 P

[56] References Cited

U.S. PATENT DOCUMENTS

| | | | |
|---|---|---|---|
| 4,215,077 | 7/1980 | Matsumoto et al. | 568/454 |
| 4,238,419 | 12/1980 | Matsumoto et al. | 568/454 |

FOREIGN PATENT DOCUMENTS

| | | | |
|---|---|---|---|
| 2715685 | 10/1977 | Fed. Rep. of Germany | 568/454 |
| 2730527 | 12/1978 | Fed. Rep. of Germany | 568/454 |
| 1545706 | 5/1979 | United Kingdom | 568/454 |

Primary Examiner—Werren B. Lone
Attorney, Agent, or Firm—Barry Kramer

[57] ABSTRACT

In hydroformylating an olefinic compound in an organic solvent and in the presence of a rhodium complex and a trisubstituted phosphine to give the corresponding aldehyde, at least one diphosphino compound of the following general formula (I) is added to the reaction system in a proportion of 0.20 to 5.0 equivalents per rhodium atom in the rhodium complex

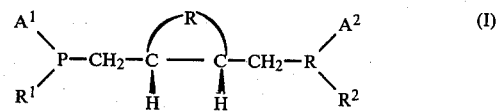

wherein $A^1$ and $A^2$, respectively, are aryl groups; $R^1$ and $R^2$, respectively, are an aryl group or a saturated hydrocarbon residue containing 1 or more carbon atoms; and

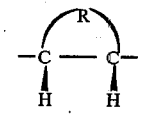

represents a substituted or unsubstituted alicyclic hydrocarbon group containing 3 to 6 carbon atoms in the main ring.

The addition of diphosphino compound (I) has a remarkable life-prolonging effect on the rhodium catalyst.

15 Claims, No Drawings

HYDROFORMYLATION OF OLEFINIC COMPOUNDS

BACKGROUND OF THE INVENTION

1. Field of the Invention

This invention relates to a method of hydroformylating olefinic compounds. More particularly, the invention relates to a method of hydroformylating an olefinic compound into the corresponding aldehyde in an organic solvent and in the presence of a rhodium complex and a trisubstituted phosphine, there being added to the reaction system at least one diphosphino compound of general formula (I)

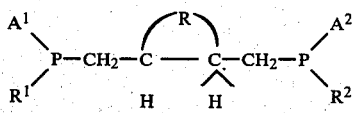

wherein $A^1$ and $A^2$, respectively, are aryl groups; $R^1$ and $R^2$, respectively, are an aryl group or a saturated hydrocarbon residue of 1 or more carbon atoms; and

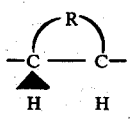

represents a substituted or unsubstituted alicyclic hydrocarbon group of 3 to 6 carbon atoms in the main ring, in a proportion of 0.20 to 5.0 equivalents per rhodium atom in said rhodium complex to thereby achieve a substantial prolongation of catalyst activity and, consequently, achieve a more advantageous hydroformylation of the olefinic compound.

2. Description of the Prior Art

There is known a hydroformylation reaction in which an olefin, exemplified by ethylene, propylene and butene, is reacted with a gaseous hydrogen-carbon monoxide mixture in an organic solvent and in the presence of a rhodium complex and a trisubstituted phosphine to obtain an aldehyde containing one more carbon atom than the starting olefin. The reaction has been commercially utilized, for example, in the production of butyraldehyde from propylene.

The rhodium complex as used for catalyzing the hydroformylation reaction is suited for industrial practice in that it helps perform the reaction under considerably milder conditions (lower temperature and pressure) than does a cobalt catalyst and that it contributes to a higher selectivity for normal-aldehyde. However, since the rhodium complex is quite expensive, the industrial value of a hydroformylation reaction with this complex depends largely on the catalyst life of the complex. Therefore, much research has heretofore been done and many proposals made in connection with means of maintaining the activity of the catalyst for an extended time under hydroformylating conditions. These methods may be roughly classified into three categories:

(1) A method in which the contemplated reaction is carried out while various reaction conditions such as the concentrations of the rhodium catalyst and trisubstituted phosphine, the partial pressure of carbon monoxide and the reaction temperature are controlled, each within a defined range, so as to suppress thermal degradation of the rhodium complex and formation of an inactive highly-carbonylated rhodium complex, e.g. see, German Patent Application (abbreviated as DTOS) 2,715,685;

(2) A method in which a small amount of oxygen is allowed to be present in the reaction system, e.g. see, DTOS 2,730,527; ;P (3) A method in which the reaction is carried out while the concentration of poisonous high-boiling byproducts in the reaction system is maintained below a certain level, e.g., see British Pat. No. 1,338,237 and British Pat. No. 1,545,706.

These hitherto-proposed methods, however, have room for improvement when industrial applications are envisaged. The first method (1) is commercially disadvantageous in that any drop in reaction temperature and any increase in concentration of the trisubstituted phosphine result in a reduced reaction rate which would require use of the expensive rhodium catalyst in an increased concentration in order to compensate for the reduction of reaction rate. With respect to the second method (2), the trisubstituted phosphine and the end product aldehyde are unstable against oxygen and tend to be converted to the substituted phosphine oxide and organic carboxylic acid, respectively, with the result that not only is the catalyst activity reduced but there are induced undesirable secondary reactions of the product aldehyde. The third method (3) is disadvantageous in that maintaining the concentration of high-boiling byproducts acting as catalyst poisons below a certain level is industrially equivalent to frequent regeneration, activation and recovery of the rhodium catalyst which are, of necessity, accompanied by losses of the rhodium catalyst and trisubstituted phosphine. Even by the above methods, a depression of catalyst activity is frequently encountered during the reaction and it has been inevitable to carry out the regeneration, activation and recovery of the rhodium catalyst with a fair frequency. This not only means a complicated procedure but also entails losses of the rhodium catalyst and trisubstituted phosphine in the regeneration step. Thus, the conventional methods for maintaining the activity of the rhodium catalyst leave much room for improvement.

SUMMARY OF THE INVENTION

The present inventors have previously found that the above-mentioned problems relating to the hydroformylation of olefinic compounds can be solved very effectively by adding a diphosphinoalkane compound of the following general formula in combination with a trisubstituted phosphine to the hydroformylation reaction system:

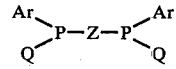

wherein Ar is an aryl group, Q is an aryl group or a saturated hydrocarbon residue containing one or more carbon atoms; and Z is a lower-alkyl-substituted or unsubstituted alkylene group whose principal chain contains 2 to 5 carbon atoms (cf. Japanese Patent Application No. 44611/78).

Further research undertaken by the present inventors in the above regard led to the finding that when a diphosphino compound of the following general formula (I) is used as said diphosphinoalkane to be added in combination with a trisubstituted phosphine, the activity life of the rhodium catalyst is significantly prolonged and, at the same time, the selectivity of the reaction (ratio of formation of normal aldehyde to branched-chain aldehyde) is further increased:

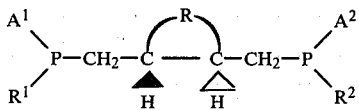

wherein $A^1$ and $A^2$ respectively, are an aryl group; $R^1$ and $R^2$, respectively, are an aryl group or a saturated hydrocarbon residue of 1 or more carbon atoms; and

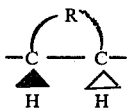

represents a substituted or unsubstituted alicyclic hydrocarbon group of 3 to 6 carbon atoms in the main ring.

As a result, in accordance with this invention, the normal aldehyde which is more useful can be obtained with high selectivity and, moreover, the concentration of substituted phosphine can be lower than the concentration level conventionally employed. Accordingly, even when the reaction is conducted at a lower reaction temperature, the reaction rate can be increased without increasing the concentration of the rhodium catalyst. Moreover, the reaction at a reduced temperature suppresses formation of undesirable high-boiling by-products, with the result that not only is the catalyst activity stabilized for an extended time period but the frequency of regeneration (recovery) is reduced so that the loss of rhodium and trisubstituted phosphine in the regeneration step may be minimized.

U.S. Pat. No. 4,139,565 states that if a hydroformylation reaction is conducted in the co-presence of a rhodium catalyst and a diphosphino compound such as trans-1,2-bis(diphenylphosphinomethyl)cyclopropane or trans-1,2-bis(diphenylphosphinomethyl)cyclobutane, satisfactory results as to reaction rate and selectivity are obtained even without using a trisubstituted phosphine such as triphenylphosphine and, therefore, that said diphosphino compound is useful as a substitute for a trisubstituted phosphine. However, the above-mentioned feature of this invention, i.e. the prolongation of catalyst life, can be implemented only by a combination of an excess of trisubstituted phosphine, relative to rhodium complex, with a certain kind of diphosphino compound in a very limited quantity range. This invention is different from the method described in the above-mentioned literature in that the former comprises a combined use of a trisubstituted phosphine and a diphosphino compound. Thus, as will be shown in Example for Comparison 2 which appears hereinafter, the reaction in the presence of a mere combination of a rhodium catalyst with a diphosphino compound suffers a considerable degradation of catalyst activity and does not always yield a satisfactory ratio of normal aldehyde.

DETAILED DESCRIPTION OF THE INVENTION

Referring to general formula (I) representing the diphosphino compound to be employed according to this invention, the aryl groups $A^1$ and $A^2$ as well as the aryl groups included within $R^1$ and $R^2$ mean aryl groups such as unsubstituted phenyl and naphthyl, as well as phenyl, naphthyl and their equivalents such as tolyl, xylyl, and the like, which may be substituted by groups inert to the reaction, e.g. lower alkyl, lower alkoxy, and the like. The saturated hydrocarbon residues for $R^1$ and $R^2$, each of which may be a saturated hydrocarbon residue containing 1 or more carbon atoms, include, for example, methyl, ethyl, propyl, butyl, pentyl, hexyl, heptyl, octyl, cyclohexyl, and the like. The formula

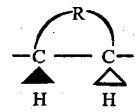

represents a substituted or unsubstituted alicyclic hydrocarbon group whose main ring contains 3 to 6 carbon atoms. The unsubstituted alicyclic hydrocarbon groups include cycloalkylene groups having a 3 to 6 membered ring such as cyclopropylene, cyclobutylene, cyclopentylene and cyclohexylene. The substituted alicyclic hydrocarbon groups include cycloalkylene groups substituted by at least one alkyl group containing up to 10 carbon atoms, cycloalkylene groups whose two carbon atoms are linked through an alkylene group containing up to 20 carbon atoms and cycloalkylene groups whose adjacent two carbon atoms are constituent members of a benzene ring. Referring, further, to the general formula (I),

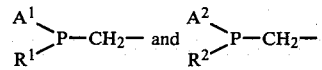

are trans-oriented with respect to said alicyclic hydrocarbon group. As preferred examples of said diphosphino compound, there may be mentioned trans-1,2-bis(diphenylphosphinomethyl) cyclopropane, trans-1,2-bis(diphenylphosphinomethyl)cyclobutane, trans-1,2-bis(diphenylphosphinomethyl)cyclopentane, trans-1,2-bis(octylphenylphosphinomethyl)cyclobutane, trans-1,2-bis(diphenylphosphinomethyl)-trans-decalin, trans-2,3-bis(diphenylphosphinomethyl)-bicyclo[2,2,2]octane, trans-9,10-bis(diphenylphosphinomethyl)-9,10-dihydrophenanthrene, and the like. Among the above-mentioned groups, trans-1,2-bis(diphenylphosphinomethyl)cyclobutane is particularly preferred from the standpoint of availability, catalyst life prolonging effect and chemical stability.

The above-mentioned diphosphino compounds may be employed singly or as a mixture of two or more thereof.

In the practice of this invention, said diphosphino compound is used in a proportion of 0.20 to 5.0 equivalents, preferably 0.25 to 3.5 equivalents, based on each gram-atom of rhodium in the rhodium complex. If the amount of diphosphino compound is less than 0.20 equivalent per gram-atom of rhodium, the addition of the diphosphino compound does not manifest its effect in any substantial measure, while the addition of more than 5.0 equivalents of the diphosphino compound per gram-atom of rhodium is undesirable because it would then cause a decrease in catalyst activity. The hydroformylation of olefinic compounds on an industrial scale is preferably carried out in a continuous process. Such a reaction is preferably conducted while the diphosphino compound is fed continuously or intermittently so that the concentration of diphosphino compound in the reaction system will be held substantially constant.

In accordance with this invention, it is essential, as aforesaid, to employ an excess of a trisubstituted phosphine, with respect to the rhodium complex, along with said diphosphino compound. The addition of said trisubstituted phosphine is beneficial to selectivity of reaction (especially, selectivity to normal aldehyde) and catalyst life. The proportion of the trisubstituted phosphine is 10 to 500 equivalents per gram-atom of rhodium in said rhodium complex and, more desirably, 25 to 300 equivalents on the same basis.

Many trisubstituted phosphines are known which can be employed for the purposes of this invention but in terms of catalyst activity, reaction selectivity and catalyst life, triarylphosphines, triarylphosphites, alkydiarylphosphines, and the like are preferred and, more specifically, triphenylphosphine, trinaphthylphosphine, tritolylphosphine, triphenylphosphite and propyldiphenylphosphine are most desirable.

The rhodium complex to be employed in the method of this invention may be any rhodium complex having an activity to catalyze hydroformylation. A large number of such rhodium complexes are known but such rhodium complexes as $HRh(CO)(PR_3)_3$ wherein R is alkyl or aryl and rhodium carbonyl clusters are especially desirable in terms of catalyst activity, the solubility and ease of use of the catalyst, and the like. As typical examples of such rhodium complexes, there may be mentioned $HRh(CO)$ $[P(C_6H_5)_3]_3$, $HRh(CO)$ $[P(C_6H_4CH_3)_3]_3$, $Rh_4(CO)_{12}$ and $Rh_6(CO)_{16}$.

As to the manner of addition of the rhodium complex, there can be used a method which comprises preparing a catalyst solution in an independent vessel in the conventional manner and feeding the solution to the hydroformylation reaction vessel.

In the practive of this invention, the concentration of the rhodium complex in the reaction system is preferably in the range of 0.05 to 5.0 milligram-atom/l as rhodium metal. If the concentration level of the rhodium complex is less than 0.05 milligram-atom/l and especially below 0.025 milligram-atom/l, the reaction rate is seriously reduced. On the other hand, the use of the rhodium complex at a level exceeding 5.0 milligram-atom/l is not only uneconomical but also causes a reduction of catalyst life.

The olefinic compounds to which the method of this invention is applicable are those containing up to 6 carbon atoms, such as ethylene, propylene, 1-butene, isobutene, 1-pentene, 1-hexene, allyl alcohol, allyl methyl ether, and the like.

The organic solvent mentioned hereinbefore may be any organic solvent that is capable of dissolving the rhodium complex, trisubstituted phosphine and diphosphino compound and will not interfere with hydroformylation. For industrial operations, it is economically advantageous to employ the product aldehyde or its condensation byproducts. Other suitable solvents include aromatic hydrocarbons such as benzene, toluene, xylene, dodecylbenzene, and the like; alicyclic hydrocarbons such as cyclohexane; ethers, ketones; esters; and the like.

The hydroformylation reaction according to this invention is carried out by feeding carbon monoxide gas and hydrogen gas into an organic solvent containing the rhodium complex, trisubstituted phosphine, diphosphino compound and olefinic compound.

In this invention, the reaction temperature is an important factor because it governs both the reaction rate and catalyst life. The reaction is desirably conducted in the temperature range of 50° to 120° C., and more desirably at 60° to 105° C. At temperatures below about 50° C., the reaction rate is too slow, while the catalyst life is too short if the reaction is carried out at temperatures over about 120° C.

In the practice of this invention, the partial pressure ratio of hydrogen to carbon monoxide is desirably within the range of 1:2 to 10:1 as the feed mixed gas, and to attain an adequate reaction rate, an adequate reaction selectivity and a sufficiently long catalyst life, it is important to ensure that, during the progress of reaction, the absolute partial pressure of carbon monoxide in the reaction system will lie between 0.1 and 2.5 atmospheres. When the absolute partial pressure of carbon monoxide is higher than about 2.5 atmospheres, the relative yield of branched aldehyde is increased and the catalyst life is shortened. Where the olefinic compound employed is gaseous at atmospheric temperature and pressure, it is industrially advantageous to ensure that the total pressure of olefin, hydrogen and carbon monoxide will be 5 to 30 atmospheres.

The reaction system can also include other gases inert to hydroformylation, if desired, such as nitrogen, helium, argon, methane, ethane, propane, butane, and the like.

The hydroformylation reaction according to this invention is desirably carried out by a continuous method in a stirred reaction vessel or a columnar reaction vessel.

The aldehydes produced by the above reaction can be separated from the reaction mixture by procedures well known in the art. The aldehydes with comparatively low-boiling points are mainly taken out from the reaction system along with the off gas, while high-boiling aldehydes are separated by depressurizing the dissolved gas and subjecting it to distillation.

Water-soluble aldehydes such as hydroxybutraldehyde which is obtainable by the hydroformylation of allyl alcohol, for example, can be advantageously extracted with an aqueous extractant.

This invention will be further described by way of the following examples. These examples are for illustrative purposes only and are not to be construed as imposing any limitation on the spirit or scope of the invention. Unless otherwise specified, all percentages and parts are by weight.

In each of the following examples and examples for comparison, the reaction was conducted in a one-liter stainless steel autoclave equipped with a magnetic stirrer, thermometer, gas inlet and gas outlet.

EXAMPLE 1

The autoclave was charged with a mixture of 150 ml of n-butyraldehyde and 250 ml of dioctyl phthalate containing 0.60 mmole of $HRh(CO)(PPh_3)_3$ (Ph=phenyl), 40 mmoles of triphenylphosphine and 0.60 mmole of trans-1,2-bis(diphenylphosphinomethyl)cyclobutane dissolved therein. The autoclave was sufficiently purged with hydrogen/carbon monoxide gas mixture (mol. ratio, 2:1) and the internal temperature was maintained at 85° C. Then, propylene, carbon monoxide, hydrogen and nitrogen gases were introduced from the gas inlet at flow rates of 30 l/hr., 20 l/hr., 40 l/hr. and 140 l/hr., respectively, and the reaction gas was purged so that the internal pressure of the autoclave was held at 15 atmospheres (absolute pressure) by means of a pressure-regulating valve provided in the gas outlet tube. The product butyraldehydes (isobutyraldehyde and n-butyraldehyde) were continuously withdrawn from the reactor along with the off gas. It was confirmed with a level gauge fitted to the autoclave that the volume of liquid in the reactor was constant after steady state had been established. The gas emerging from the reactor was thoroughly bubbled into toluene cooled with dry ice-acetone, and the product butyraldehydes were trapped and analyzed by gas chromatography. The gas emerging from the reactor was also analyzed by gas chromatography to determine the proportions of carbon monoxide, hydrogen, propylene and propane in the emergent gas.

Table 1 shows the rates of formation of n-butyraldehyde and isobutyraldehyde at 20 hours and 170 hours after the start of the reaction. The fact that the rate of formation of butyraldehyde after 170 hours of reaction was substantially equal to that after 20 hours indicates that the catalyst activity has been sustained without any significant decrease throughout the reaction.

EXAMPLE 2

The reaction procedure described in Example 1 was repeated except that 0.90 mmole of trans-1,2-bis(diphenylphosphinomethyl)cyclobutane was employed. Table 1 shows the rates of formation of n-butyraldehyde and isobutyraldehyde at 20 hours and 170 hours after the start of the reaction.

EXAMPLE 3

The reaction procedure described in Example 1 was repeated except that 0.75 mmole of $HRh(CO)(PPh_3)_3$, 50 mmoles of triphenylphosphine and 0.90 mmole of trans-1,2-bis(diphenylphosphinomethyl)cyclopentane were used. Table 1 shows the rates of formation of n-butyraldehyde and isobutyraldehyde after 20 hours and 170 hours of reaction.

EXAMPLE 4

A mixture of 100 ml of propionaldehyde and 300 ml of dioctyl phthalate containing 0.15 mmole of $Rh_6(CO)_{16}$, 90 mmoles of triphenylphosphine and 0.6 mmole of trans-1,2-bis(diphenylphosphinomethyl)cyclobutane dissolved therein was used as a catalyst solution and the internal temperature of the reactor was maintained at 70° C. As in Example 1, ethylene, carbon monoxide, hydrogen and nitrogen gases were introduced at rates of 45 l/hr., 30 l/hr., 60 l/hr. and 85 l/hr., respectively, and the internal pressure of the reactor was kept at 13 atmospheres (absolute pressure). The rates of formation of propionaldehyde at 20 hours and 170 hours after the start of the reaction were 0.991 mole and 0.980 mole, respectively, per hour.

EXAMPLE FOR COMPARISON 1

The reaction procedure of Example 1 was repeated except that trans-1,2-bis(diphenylphosphinomethyl)cyclobutane was not added at all.

Table 1 shows the rates of formation of n-butyraldehyde and isobutyraldehyde at 20 and 170 hours after the start of the reaction. It will be apparent that, compared with the results obtained in Example 1, the rate of formation of aldehyde was significantly lower and that the ratio of n-aldehyde to the total product aldehyde was low.

EXAMPLE FOR COMPARISON 2

The reaction procedure of Example 1 was repeated except that triphenylphosphine was not added at all. Gas chromatographic determinations of carbon monoxide and propylene in the emergent gas showed that the progress of the reaction was very fast in the period immediately following the start of the reaction but due to a marked decrease of catalyst activity, the rates of formation of n-butyraldehyde and isobutyraldehyde after 20 hours of reaction were as low as 0.389 mole/hr. and 0.108 mole/hr., respectively.

It is obvious that, compared with the results of Example 1, the omission of trisubstituted phosphine resulted in a marked decrease of catalyst activity and a low relative yield of n-butyraldehyde.

EXAMPLE FOR COMPARISON 3

The reaction procedure of Example 1 was repeated except that 0.06 mmole of trans-1,2-bis(diphenylphosphinomethyl)cyclopentane was employed. Table 1 shows the rates of formation of n-butyraldehyde and isobutyraldehyde at 20 and 170 hours after the start of the reaction.

EXAMPLE FOR COMPARISON 4

The reaction procedure of Example 1 was repeated except that 6.0 mmoles of trans-1,2-bis(diphenylphosphinomethyl)cyclobutane was employed. Table 1 shows the rates of formation of n-butyraldehyde and isobutyraldehyde at 20 hours and 170 hours after the start of the reaction.

TABLE I

| | Rates of formation of butyraldehydes (mole/hr.) | | | |
| --- | --- | --- | --- | --- |
| | After 20 hrs. | | After 170 hrs. | |
| | n-Butyraldehyde | Isobutyraldehyde | n-Butyraldehyde | Isobutyraldehyde |
| Example 1 | 0.634 | 0.056 | 0.627 | 0.055 |
| Example 2 | 0.590 | 0.050 | 0.581 | 0.049 |
| Example 3 | 0.717 | 0.063 | 0.694 | 0.060 |
| Example for Comparison 1 | 0.628 | 0.067 | 0.460 | 0.049 |
| Example for Comparison 3 | 0.619 | 0.066 | 0.487 | 0.052 |
| Example for Comparison 4 | 0.278 | 0.023 | 0.269 | 0.022 |

EXAMPLE 5

The autoclave was charged with 320 ml of a toluene solution containing 0.60 mmole of $HRh(CO)(PPh_3)_3$, 60 mmoles of triphenylphosphine and 0.525 mmole of trans-1,2-bis(diphenylphosphinomethyl)cyclobutane. The atmosphere in the autoclave was thoroughly purged with nitrogen gas and, then, with hydrogen/carbon monoxide (mol. ratio, 2:1) and the autoclave was heated to a constant temperature of 65° C. Then, a gaseous mixture of hydrogen and carbon monoxide (mol. ratio, 2:1) was introduced into the autoclave, and utilizing this gas, the internal pressure was controlled to 3.0 atmospheres (absolute pressure) and the flow rate of emergent gas to 20 Nl/hr. By means of a constant-speed pump, a total of 80 ml of allyl alcohol was introduced under stirring at the rate of 40 ml/hr. over a period of 2 hours. After the feed of allyl alcohol was terminated, the reaction was further continued for 2 hours. The emergent gas was thoroughly guided into a toluene trap cooled with dry ice-acetone and the accompanying allyl alcohol, propionaldehyde and other low-boiling products were thus collected in the above toluene trap. The hydroformylation of allyl alcohol was thus conducted at constant pressure and temperature for 4 hours. Gas chromatographic analysis of the reaction mixture and of the liquid in the toluene trap showed that there was 0.035 mmole of unreacted allyl alcohol (% conversion of allyl alcohol=97%). The yields of propionaldehyde, n-propanol, 2-methyl-3-hydroxy-propionaldehyde and 4-hydroxybutyraldehyde were 0.080 mole, 0.034 mole, 0.114 mole and 0.856 mole, respectively.

The internal temperature of the autoclave was reduced to room temperature and the autoclave was decompressed. The reaction mixture was then transferred to a one-liter separatory funnel equipped with agitator means, care being exercised to prevent exposure of the mixture to atmospheric air. At room temperature and in a hydrogen gas atmosphere, the unreacted alcohol and reaction products in the reaction mixture were extracted twice with 400 ml of distilled water. The residual toluene solution containing the catalyst components was charged into the autoclave and the hydroformylation reaction of allyl alcohol was conducted as described above for 4 hours. After the reaction, the unreacted allyl alcohol and reaction product were extracted out from the reaction mixture. The above procedure was repeated for a total of 10 times. Table 2 shows the yields of propionaldehyde, n-propanol, 2-methyl-3-hydroxypropionaldehyde and 4-hydroxybutyraldehyde after the 5th and 10th reactions.

TABLE 2

| Reaction | Product | | | |
|---|---|---|---|---|
| | Propionaldehyde (mole) | n-Propanol (mole) | 2-Methyl-3-hydroxy-propionaldehyde (mole) | 4-Hydroxy-butyralde-hyde (mole) |
| 5 th | 0.078 | 0.033 | 0.112 | 0.840 |
| 10 th | 0.077 | 0.032 | 0.111 | 0.823 |

EXAMPLE 6

The autoclave was charged with a dodecylbenzene solution containing 0.80 mmole of HRh(CO)(PPh$_3$)$_3$, 50 mmoles of triphenylphosphine and 0.80 mmole of trans-1,2-bis(diphenylphosphinomethyl)cyclobutane. The internal atmosphere of the autoclave was thoroughly purged with nitrogen gas and, then, with hydrogen/carbon monoxide (mol. ratio, 3:1) and the internal temperature was elevated to 90° C. At this constant temperature, hydrogen/carbon monoxide gas (mol. ratio, 3:1) was introduced into the autoclave, and by utilizing this mixed gas, the internal pressure of the autoclave was controlled to 3.0 atmospheres (absolute pressure) and the flow rate of emergent gas to 20 Nl/hr. By means of a constantspeed pump, a total of 90 ml of 1-pentene was introduced under stirring at the rate of 45 ml/hr. over a period of 2 hours. After the introduction of 1-pentene was terminated, the reaction was further continued for 2 hours. The emergent gas was thoroughly guided into a toluene trap cooled with dry ice-acetone and the accompanying 1-pentene and reaction products were thus collected in the same trap. The hydroformylation of 1-pentene was thus carried out at constant temperature and pressure for 4 hours. Gas chromatographic analysis of the reaction mixture and of the liquid in the toluene trap revealed that there was 0.041 mole of unreacted 1-pentene (% conversion of 1-pentene, 95%). The yields of n-pentane, 2-pentane, 2-methylpentanal and n-hexanal were 0.0151 mole, 0.0312 mole, 0.0547 mole and 0.679 mole, respectively.

The autoclave was decompressed while the internal temperature was reduced to 50° C., and at this temperature the distillation was carried out for about 1 hour while the degree of depressurization was varied according to the distillation rate. The residual dodecylbenzene solution containing the catalyst components was charged into the autoclave and the hydroformylation of 1-pentene was carried out in the same manner as described above for 4 hours. The unreacted 1-pentene and reaction products were separated after the reaction. The above procedure was repeated for a total of 10 times. Table 3 shows the yields of unreacted 1-pentene and various reaction products after the 5th and 10th reactions.

TABLE 3

| Reaction | Product | | | | |
|---|---|---|---|---|---|
| | Unreacted 1-pentene (mole) | n-Pentene (mole) | 2-Pentene (mole) | 2-Methyl-pentanal (mole) | n-Hex-anal (mole) |
| 5th | 0.0535 | 0.0153 | 0.0307 | 0.0538 | 0.668 |
| 10th | 0.0715 | 0.0200 | 0.0225 | 0.0528 | 0.653 |

We claim:

1. A process for hydroformylating an olefinic compound in an organic solvent to obtain the corresponding aldehyde, which comprises treating said olefinic compound with gaseous carbon monoxide and hydrogen in the presence of a rhodium complex, 10 to 500 equivalents per gram-atom of rhodium in said rhodium complex of a trisubstituted phosphine and 0.20 to 5.0 equivalents per gram-atom of rhodium in said rhodium complex of at least one diphosphino compound of the general formula (I)

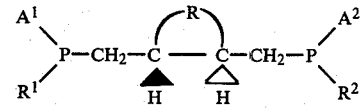

wherein $A^1$ and $A^2$, respectively, are aryl groups; $R^1$ and $R^2$, respectively, are an aryl group or a saturated hydrocarbon residue containing 1 or more carbon atoms; and

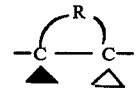

represents a substituted or unsubstituted alicyclic hydrocarbon group containing 3 to 6 carbon atoms in the main ring, said aryl group, in each instance, being selected from the group consisting of phenyl, naphthyl, tolyl and xylyl, which may be unsubstituted or substituted by lower alkyl or lower alkoxy.

2. A hydroformylation process as claimed in claim 1 wherein the concentration of said rhodium complex in the reaction system is 0.05 to 5.0 milligram-atom/liter as rhodium metal.

3. A hydroformylation process as claimed in claim 1 wherein said rhodium complex is a compound of the general formula HRh(CO)(PR$_3$)$_3$ wherein R is alkyl or aryl, or a rhodium carbonyl cluster.

4. A hydroformylation process as claimed in claim 3 wherein said rhodium complex is HRh(CO)[P(C$_6$H$_5$)$_3$]$_3$, HRh(CO) [P(C$_6$H$_4$CH$_3$)$_3$]$_3$, Rh$_4$(CO)$_{12}$ or Rh$_6$(CO)$_{16}$.

5. A hydroformylation process as claimed in claim 1 wherein said olefinic compound is an olefinic compound containing up to 6 carbon atoms.

6. A hydroformylation process as claimed in claim 5 wherein said olefinic compound is ethylene, propylene, 1-butene, isobutene, 1-pentene, 1-hexene, allyl alcohol or allyl methyl ether.

7. A hydroformylation process as claimed in claim 1 wherein said diphosphino compound is trans-1,2-bis(diphenylphosphinomethyl)cyclopropane, trans-1,2-bis(diphenylphosphinomethyl)cyclobutane, trans-1,2-bis(diphenylphosphinomethyl)cyclopentane, trans-1,2-bis(octylphenylphosphinomethyl)cyclobutane, trans-1,2-bis(-diphenylphosphinomethyl)-trans-decalin, trans-2,3-bis(-diphenylphosphinomethyl)-bicyclo[2,2,2]octane or trans-9,10-bis(diphenylphosphinomethyl)-9,10-dihydrophenanthrene.

8. A hydroformylation process as claimed in claim 7 wherein said diphosphino compound is trans-1,2-bis(diphenylphosphinomethyl)cyclobutane.

9. A hydroformylation process as claimed in claim 1 wherein said trisubstituted phosphine is a triarylphosphine, triarylphosphite or alkyldiarylphosphine.

10. A hydroformylation process as claimed in claim 9 wherein said trisubstituted phosphine is triphenylphosphine, trinaphthylphosphine, tritolylphosphine, triphenylphosphite or propyldiphenylphosphine.

11. A hydroformylation process as claimed in claim 1 wherein said diphosphino compound is used in a proportion of 0.25 to 3.5 equivalents per gram-atom of rhodium in said rhodium complex.

12. A hydroformylation process as claimed in claim 1 wherein the hydroformylation of said olefin is carried out at a reaction temperature of 50° to 120° C.

13. A hydroformylation process as claimed in claim 1 wherein the partial pressure ratio of hydrogen and carbon monoxide is 1:2 to 10:1 as the feed mixed gas.

14. A hydroformylation process as claimed in claim 13, wherein the absolute partial pressure of carbon monoxide in the reaction system is 0.1 to 2.5 atmospheres.

15. A hydroformylation process as claimed in claim 1 wherein said organic solvent is the product aldehyde, a condensation product thereof, an aromatic hydrocarbon, alicyclic hydrocarbon, ether, ketone or ester.

* * * * *

UNITED STATES PATENT AND TRADEMARK OFFICE
CERTIFICATE OF CORRECTION

PATENT NO. : 4,306,087
DATED : December 15, 1981
INVENTOR(S) : MITSUO MATSUMOTO ET AL It is certified that error appears in the above-identified patent and that said Letters Patent is hereby corrected as shown below:

On The Title Page,

Abstract, line 8, 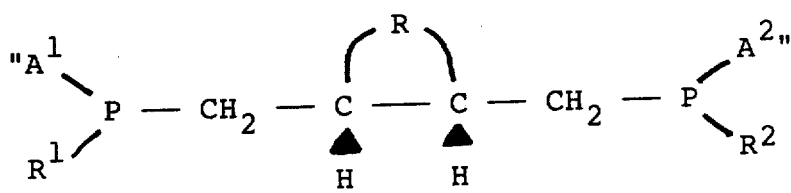

should be read as

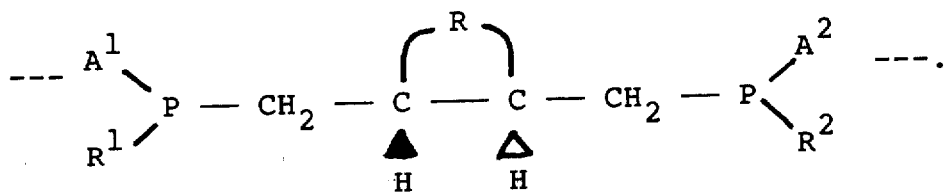 ---.

UNITED STATES PATENT AND TRADEMARK OFFICE
CERTIFICATE OF CORRECTION

PATENT NO. : 4,306,087

DATED : December 15, 1981

INVENTOR(S) : MITSUO MATSUMOTO ET AL

It is certified that error appears in the above-identified patent and that said Letters Patent is hereby corrected as shown below:

Abstract, line 13, " 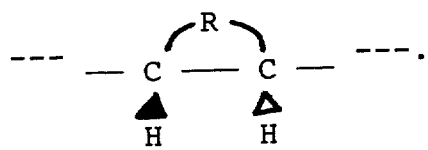 " should be read as $$--- -C\overset{H}{\underset{\blacktriangle}{}}\overbrace{\phantom{-}R\phantom{-}}C\overset{H}{\underset{\triangle}{}}- ---.$$

Column 1, lines 16-19, $$"A^1{\underset{R^1}{\diagdown}}P-CH_2-C\overset{H}{\underset{\blacktriangle}{}}\overbrace{\phantom{-}R\phantom{-}}C\overset{H}{\underset{\wedge}{}}-C-CH_2-P{\underset{R^2}{\diagup}}A^2\ " \quad \text{should be}$$

read as $--- A^1{\underset{R^1}{\diagdown}}P-CH_2-C\overset{H}{\underset{\blacktriangle}{}}\overbrace{\phantom{-}R\phantom{-}}C\overset{H}{\underset{\triangle}{}}-CH_2-P{\underset{R^2}{\diagup}}A^2 ---.$

UNITED STATES PATENT AND TRADEMARK OFFICE
CERTIFICATE OF CORRECTION

PATENT NO. : 4,306,087
DATED : December 15, 1981
INVENTOR(S) : MITSUO MATSUMOTO ET AL It is certified that error appears in the above-identified patent and that said Letters Patent is hereby corrected as shown below:

Column 1, lines 26-29, " 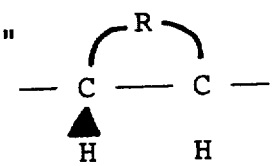 " should be read as --- 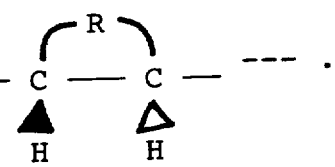 --- .

Claim 1 (column 10, lines 50-53), " 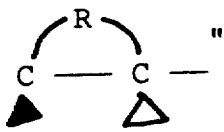 " should be read as --- 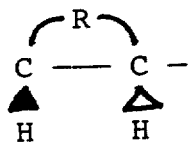 --- .

Signed and Sealed this

Twenty-sixth Day of October 1982

[SEAL]

Attest:

GERALD J. MOSSINGHOFF

Attesting Officer      Commissioner of Patents and Trademarks